US008208346B2

(12) United States Patent
Crunkilton

(10) Patent No.: US 8,208,346 B2
(45) Date of Patent: Jun. 26, 2012

(54) SELECTABLE TUNING TRANSFORMER

(75) Inventor: Jeff Crunkilton, Everett, WA (US)

(73) Assignee: LipoSonix, Inc., Bothell, WA (US)

(*) Notice: Subject to any disclaimer, the term of this patent is extended or adjusted under 35 U.S.C. 154(b) by 317 days.

(21) Appl. No.: 12/730,023

(22) Filed: Mar. 23, 2010

(65) Prior Publication Data
US 2010/0263197 A1 Oct. 21, 2010

Related U.S. Application Data

(60) Provisional application No. 61/162,676, filed on Mar. 23, 2009.

(51) Int. Cl.
H04R 31/00 (2006.01)
A61B 8/00 (2006.01)

(52) U.S. Cl. .................................................. 367/138
(58) Field of Classification Search .................. 367/138, 367/137, 13
See application file for complete search history.

(56) References Cited

U.S. PATENT DOCUMENTS

| 3,934,577 | A | 1/1976 | Romani |
|---|---|---|---|
| 4,718,428 | A | 1/1988 | Russell |
| 5,050,613 | A | 9/1991 | Newman et al. |
| 5,198,713 | A | 3/1993 | Suzuta |
| 5,313,947 | A | 5/1994 | Micco |
| 5,603,324 | A | 2/1997 | Oppelt et al. |
| 6,104,670 | A | 8/2000 | Hossack et al. |
| 6,178,342 | B1 | 1/2001 | Borgos et al. |
| 6,480,796 | B2 | 11/2002 | Wiener |
| 6,592,525 | B2 | 7/2003 | Miller et al. |
| 6,612,987 | B2 | 9/2003 | Morsy et al. |
| 7,356,905 | B2 | 4/2008 | Ketterling et al. |
| 7,741,753 | B2 | 6/2010 | Puskas |
| 7,993,289 | B2 | 8/2011 | Quistgaard et al. |
| 2004/0202049 | A1 | 10/2004 | Breed et al. |
| 2008/0042519 | A1 | 2/2008 | Marshall et al. |
| 2010/0241034 | A1 | 9/2010 | Little |
| 2010/0249669 | A1 | 9/2010 | Ulric et al. |
| 2010/0263197 | A1* | 10/2010 | Crunkilton ................... 600/459 |
| 2011/0077557 | A1 | 3/2011 | Wing et al. |
| 2011/0077559 | A1 | 3/2011 | Quistgaard et al. |

FOREIGN PATENT DOCUMENTS

WO    WO 2005/030038 A2    4/2005

(Continued)

OTHER PUBLICATIONS

Fischer et al., "Simultaneous Measurement of Digital Artery and Skin Perfusion Pressure by the Laser Doppler Technique in Healthy Controls and Patients with Peripheral Arterial Occlusive Disease," European Journal Vasc Endovasc Surgery, vol. 10, pp. 231-236 (1995).

(Continued)

Primary Examiner — Daniel Pihulic
(74) Attorney, Agent, or Firm — Wood, Herron & Evans, LLP

(57) ABSTRACT

An assembly and method for assembling a tuning transformer (104) and printed circuit board (PCB) (108) to a transducer (110) to produce a tuned ultrasound transducer (100). The tuned ultrasound transducer allows a transducer to be made with some degree of inconsistency in its impedance magnitude and phase, but each transducer, when configured and coupled to a tuning transformer assembly, produces a signal that is substantially homogeneous.

13 Claims, 5 Drawing Sheets

FOREIGN PATENT DOCUMENTS

WO    WO 2006/031479 A1    3/2006

OTHER PUBLICATIONS

Lukkari-Rautiarinen et al., "Reproducibility of Skin Blood Flow, Perfusion Pressure and Oxygen Tension Measurements in Advanced Lower Limb Ischaemia," *European Journal Vasc Endovasc Surgery*, vol. 3, pp. 345-350 (1989).

Svilainis, L. and V. Dumbrava, "Evaluation of the Ultrasonic Transducer Electrical Matching Performance," ULTRAGARSAS (Ultrasound) Journal, vol. 62, No. 4, pp. 16-21 (2007).

* cited by examiner

SELECTABLE TUNING TRANSFORMER

CROSS REFERENCE TO RELATED APPLICATION

This application claims the benefit of U.S. Provisional Application No. 61/162,676, filed on Mar. 23, 2009, the full disclosure of which is incorporated herein by reference.

BACKGROUND

In electronics systems it is desirable to have the source (system based pulser and receiver) and load (transducer) impedances be controlled.

1) To optimize power transfer to a transducer it is necessary to have the transducer match the complex conjugate impedance characteristics of the system.

2) To minimize reflections in the transmission line between the system and transducer, it is necessary to match the transducer impedance to the transmission line impedance.

3) To minimize output power variation, it is desirable to have a consistent transducer and system so that power transfer variation is minimized.

Ideally, for an ultrasound system, the source impedance has a controlled characteristic impedance with a phase angle of zero degrees. A cable that matches that impedance is used to connect the source to the transducer. Typical values for the impedances are 50-100 ohms. However, a piezoelectric element by itself will typically have an impedance that is very different from this, and that varies significantly from unit to unit.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Described herein are methods for forming a tuned ultrasound transducer assembly and assembling the tuned ultrasound transducer assembly to a medical device. The medical device has a system side. The method includes selecting a transformer having more than one inductance value and more than one voltage gain value, at least one of which is appropriate to the operation of a transducer. The transducer has a ceramic side. The transformer has a first set of tap lines on a first side of the transformer, and a second set of tap lines on a second side of the transformer. Each tap line corresponds to one of the set of inductance values or voltage gain values. The method also involves connecting the transformer to a printed circuit board (PCB) having a first group of electrical leads matching the first set of tap lines of the transformer and a second group of leads matching the second set of tap lines. The method further involves connecting the medical device system side to one of the first group of leads and connecting the transducer-ceramic side to one of the second group of leads.

The method may further involve a transducer being measured for impedance magnitude and phase, and a transformer being selected having a tuning profile sufficiently close to the transducer so as to balance the transducer to a particular impedance and phase angle value. The assembly may be attached to the transducer. The transducer may be a mechanically focused high intensity ultrasound transducer. Alternatively, the transducer may be an annular, linear or 2D array.

The method may further involve opening the signal between two or more electrical leads by connecting a jumper between the leads, blowing out a block between the leads, and/or by connecting a mechanical switch between the leads.

Also described herein are ultrasound transducer tuning assemblies. The assemblies have a transformer with more than one impedance sections demarked by a like number of taps, each impedance section having a different inductance value and voltage gain value. The assembly also has a printed circuit board attached to the transformer, wherein the taps connect to a set of lands on the PCB, the PCB having a first electrical connection for receiving a first electrical signal and a second electrical connection for transmitting a second electrical signal. There is also an ultrasound transducer in electronic communication with the second electrical signal; and at least one connector for connecting two lands on the PCB to connect taps on the transformer such that the output signal of the transformer tuning assembly matches a signal profile of the ultrasound transducer.

The ultrasound transducer may be mechanically focused or an array (annular, linear or 2D). The tuning assembly may have a connector that is either a jumper or mechanical switch.

DETAILED DESCRIPTION

Figure 1A:
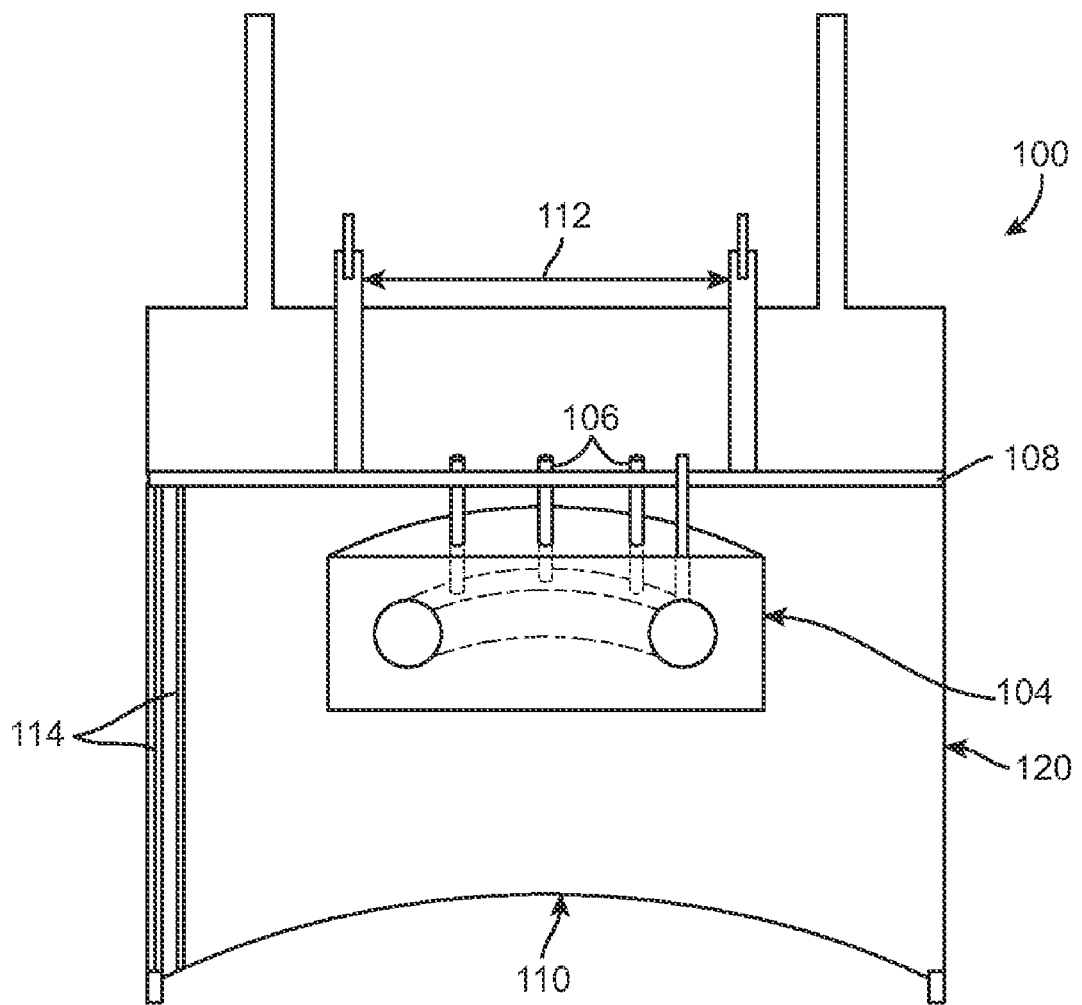
FIG. 1A shows a section view of a tuning transformer assembly in accordance with embodiments.

In the following paragraphs, various aspects and embodiments of the method and apparatus will be described. Specific details will be set forth in order to provide a thorough understanding of the described embodiments of the present invention. However, it will be apparent to those skilled in the art that the described embodiments may be practiced with only some or all of the described aspects, and with or without some of the specific details. In some instances, descriptions of well-known features may be omitted or simplified so as not to obscure the various aspects and embodiments of the present invention.

Parts of the description will be presented using terminology commonly employed by those skilled in the art to convey the substance of their work to others skilled in the art, including terms of operations performed by or components included in the system. Electronic communication refers to any intended passing of electrons from one component described herein to any other component. The transfer of electrons may be for power, signal, data or any other intended purpose (including ground).

Various operations will be described as multiple discrete steps performed in turn in a manner that is most helpful in understanding the embodiments described herein. However, the order of description should not be construed as to imply that these operations are necessarily performed in the order they are presented, or even order dependent.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Described herein are assemblies and methods for assembling a tuning transformer and printed circuit board (PCB) to produce a tuned ultrasound transducer. The tuned ultrasound transducer allows a transducer to be made with some degree of inconsistency in its impedance magnitude and phase angle. Each transducer manufactured using the methods described herein, when configured and coupled to a tuning transformer assembly, produces a signal that is substantially homogeneous. The transformer windings create a specific inductance value that would be placed in parallel with the transducer, transmission line and a voltage gain to modify the impedance and phase values.

The transducer may be formed from ceramics. For small or medium bulk quantity of the ceramics purchased, the impedance characteristics of a batch of ceramics can be very similar within the batch and from batch to batch. In an embodiment, a multiple turn transformer may be designed so that each winding has a different inductance value necessary to capture a range of impedance values that can be tuned to match the impedance values in each of the transducers in a batch of transducers. The transformer may be mounted to a circuit board (PCB) and then the windings of the transformer can be selected to provide the tuning closest to the desired impedance, for example 50 ohms magnitude, 0 degrees phase. If the batch to batch impedance values vary enough, a few transformers may be necessary to tune the entire batch, or a transformer with a wider tuning range may be used.

Transducers were measured to determine the average impedance value that would tune the batch to fifty ohms and zero degrees phase angle (50Ω/0°). The secondary winding can be used to tune the phase angle of the transducer/transformer circuit to 0°. It will also affect magnitude as seen from the system due to the turns ratio of transformer primary to secondary windings being adjusted, but the intent of the secondary winding adjustment is to tune the phase close to zero. The primary winding on the transformer can then be used to tune the impedance to 50Ω after the secondary winding has been adjusted. The transformer windings may have a plus and minus 1 winding from the nominal setting to give three separate settings for each winding. This allows a total of six separate settings available for each transformer. The PCB that the transformer mounts to provides pads for a 0Ω jumper to be soldered into the circuit to complete the connection to a given winding.

Tuning would start by an assembler soldering the jumpers at the nominal setting and taking an impedance measurement. The impedance phase angle may be adjusted by moving the secondary jumper to a different position (if required) and then adjusting the impedance magnitude by moving the primary jumper (if required). This greatly reduces the time and complexity of tuning the transducers by hand and produces an assembly that can be relatively inexpensive to manufacture.

Now turning to the drawings, a section view is provided of the tuning transformer assembly 100 in FIG. 1A. The transformer assembly 100 is shown having a transformer 104 attached to a printed circuit board 108 via a plurality of taps 106. The taps 106 extend through a like number of apertures in the PCB, and are soldered in place. A system-connection electrical path 112 is shown as a pair of pins on "top" of the board, while a transducer-ceramic electrical path 114 is shown as a second pair of pins on the "bottom" of the PCB. The orientation of top and bottom refer strictly to the orientation of the diagram on the page, and should not be construed as providing any limitation or restriction to the position of the transmit or receive paths of the transformer assembly. An ultrasound transducer 110 is connected to the transmit path 114.

The transducer 110 may be, as non-limiting examples, a mechanically focused ultrasound transducer (having a fixed focus defined by the physical shape of the transducer), or an electronically steered (annular, linear or 2D) array.

Figure 1B:
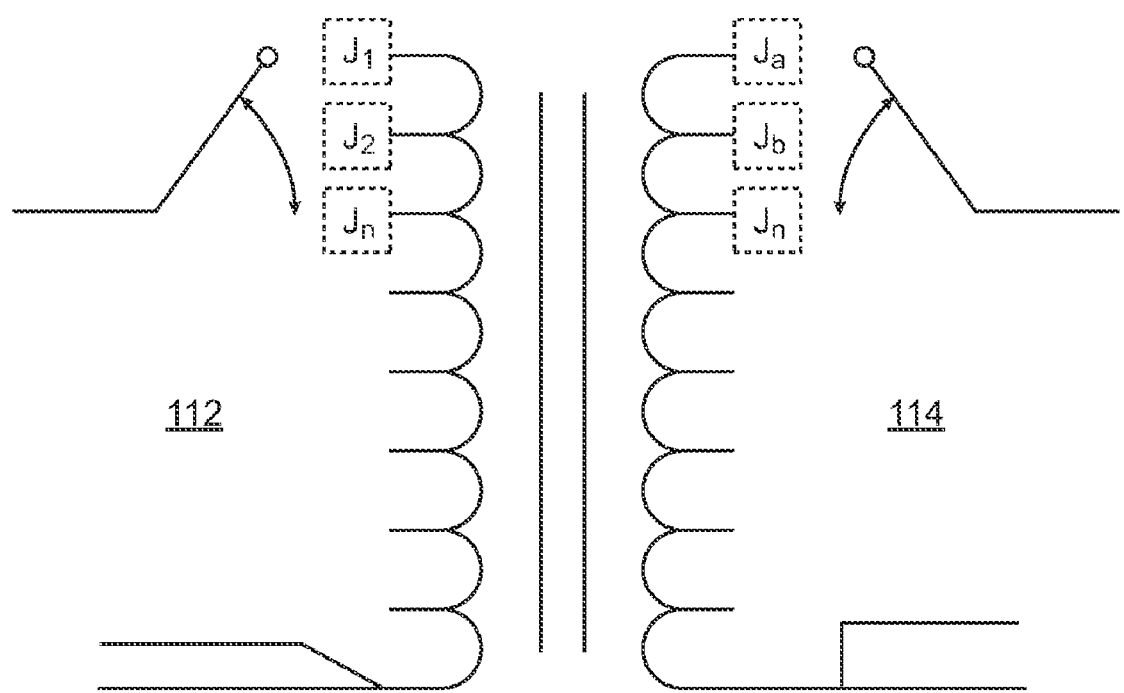
FIG. 1B is a schematic view of the transformer assembly of FIG. 1A showing a plurality of optional jumper positions on a system connection side and a second plurality of optional jumper positions on a transducer ceramic side.

Schematically, the transformer assembly 100 is shown having a plurality of optional jumper positions $J_{1-n}$ on the system connection side 112, and a second plurality of optional jumper positions $J_{a-n}$ on the transducer ceramic side 114 (FIG. 1B). When the transformer assembly 100 is produced, a jumper is identified on each side of the transformer, the connection together of which produces a transformer assembly having the proper tuning characteristics. For example, as described above, the transformer 104 may have a plus and minus 1 winding from the nominal setting to give three separate settings for each winding. This allows a total of six separate settings available for the transformer. Connections may be arranged to select separate settings, with leads from the transformer 104 extending to the PCB 108 via the taps 106. Thus, the position of the connectors J determines the tuning of the transformer. One connector is used to connect the system side 112 to one and only one of the connectors $J_{1-n}$. On the transducer-ceramic side, one connector is made between the transducer ceramic 114 electrical lead, and the desired connector $J_{a-n}$. Thus only one connection is made on each of the system side, and the transducer ceramic side. Although the illustration shows an equal number of taps on each side of the transformer, there is no requirement of numerical equivalence between one side and the other. Additional windings and taps of the transformer may be used to generate greater ranges of load compensation in the assembly. Furthermore, assignment of the primary or secondary side of the transformer with either side of the assembly is purely arbitrary. That is, the primary side of the transformer may connect with either the system side, or the transducer ceramic side.

While jumpers are provided herein as an illustrative manner to connect the electrical leads on the PCB, the use of jumpers should not be construed in any way as limiting. Connection of the electrical leads may be done through a variety of techniques and components readily available and known in the art. The leads may be connected by using mechanical switches, connected through solder bridges, by blowing out non-conductive blocks between the leads, and via other methods.

If the signal from the system side has a specific impedance and phase angle (for example being 50 ohms and 0° phase angle) and is connected directly from the system connection path 112 into the ultrasound transducer (instead of via the transformer assembly 100 as shown in FIG. 1A), the innate unmatched impedance and phase angle of the transducer ceramic could result in inefficiency and performance variation. In such a directly connected system, there may be reflections and power variability on the source electrical signal. To correct for the innate impedance and phase angle of the transducer, the transformer assembly 100 is inserted between the medical device generating the signal (i.e., at the system connection path 112), and the transducer 110. The native impedance and phase angle of the transducer 110 is measured using a meter, and the transformer assembly 100 is adjusted using the lands of the PCB as ways to connect to taps of the transducer 110 using 0 ohm jumpers. The taps 106 of the transformer 104 are of desirably known values so the transformer does not have to be evaluated in a trial and error manner. The known values allow for the jumpers to be properly placed on the system side and transducer ceramic side allowing for a highly efficient assembly and process for tuning the transducer.

Figure 2:
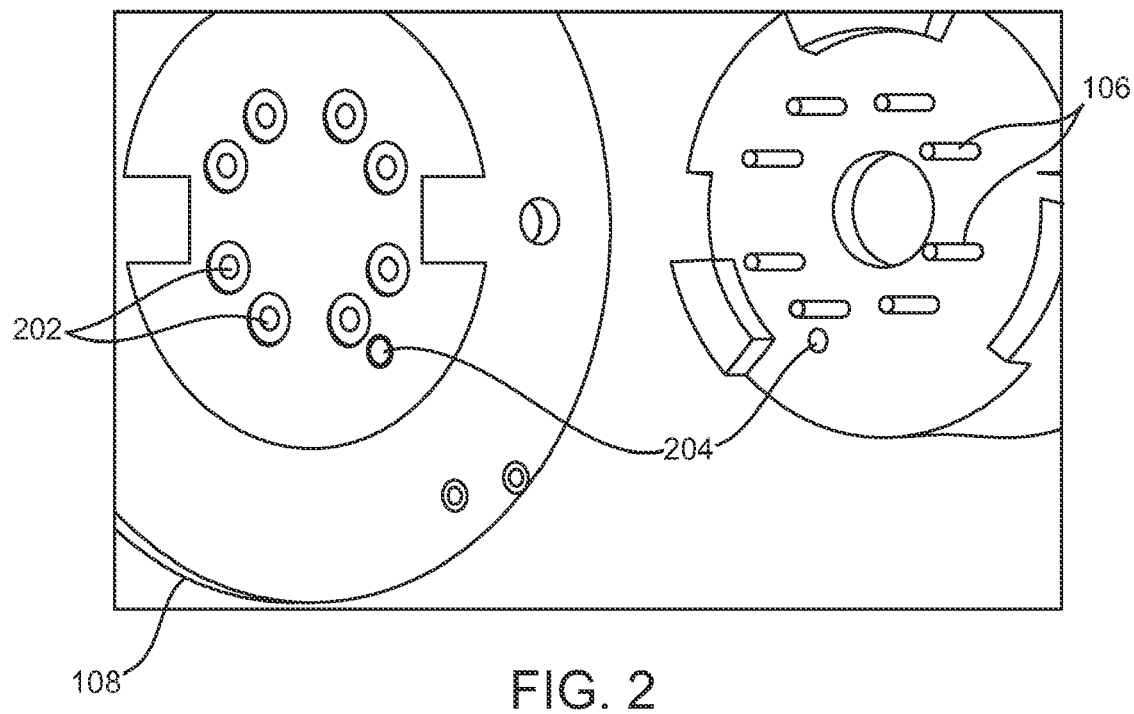
FIG. 2 shows pin indicators on a PCB that provide guidance for proper orientation of a transformer to the PCB.
Figure 3:
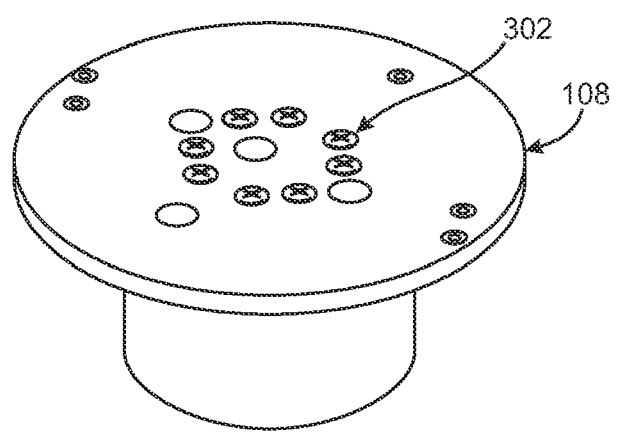
FIG. 3 illustrates taps soldered to the PCB of FIG. 2.
Figure 4:
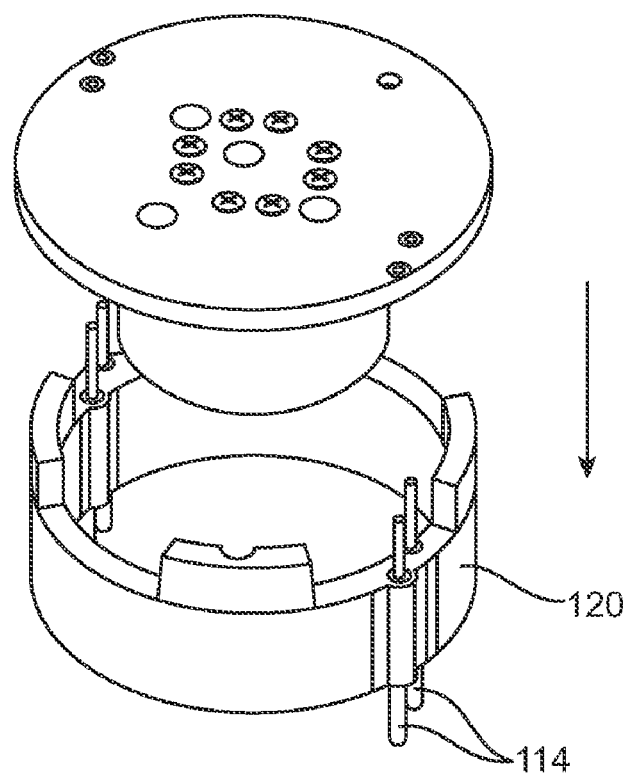
FIG. 4 illustrates the PCB laid unto a casing in accordance with an assembly step of embodiments.
Figure 5:
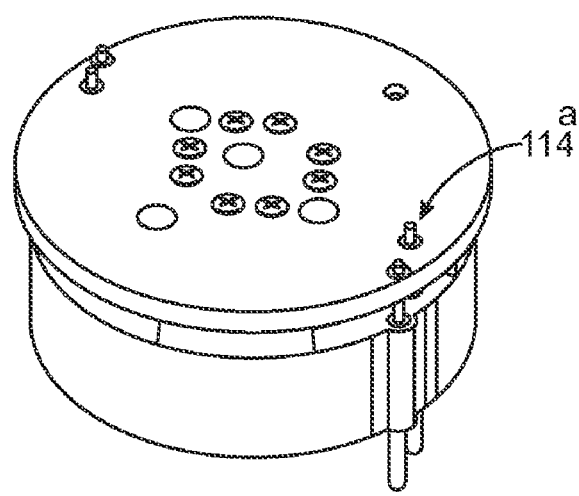
FIG. 5 shows the pins of the output signal when soldered in accordance with an assembly step of embodiments.
Figure 6:
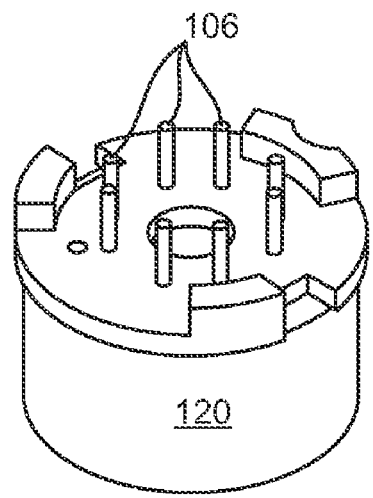
FIG. 6 illustrates a side perspective view of the transformer assembly.
Figure 7:
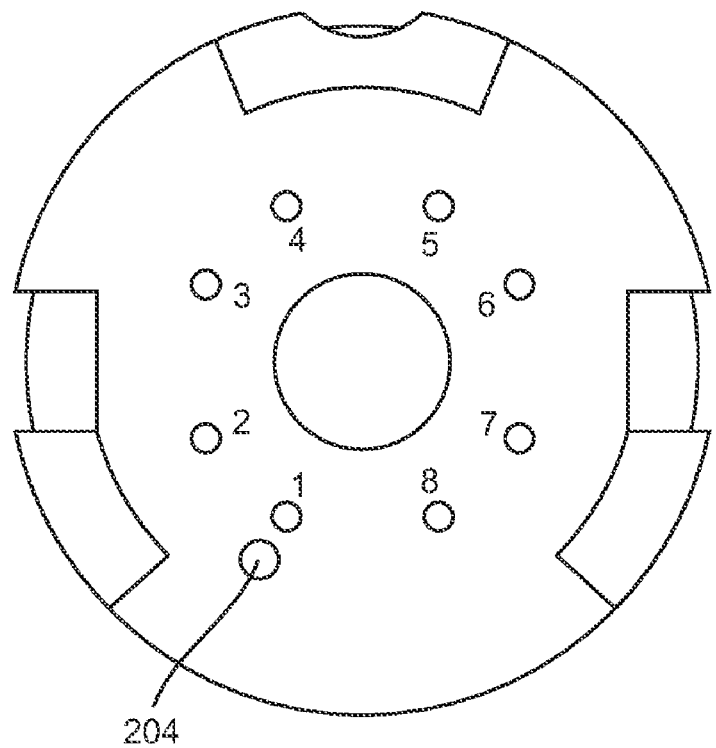
FIG. 7 shows a top view of the transformer assembly.

Pin indicators 204 on the PCB and transformer assembly provide guidance for the proper orientation of the transformer to the PCB (FIG. 2). The taps 106 are aligned to and push through the tap apertures 202 on the PCB 108. Once the taps 106 are in their proper alignment, the taps are soldered to the PCB 302 (FIG. 3). Additional apertures in the PCB may receive the output signal pins 114. The PCB is laid into the casing 120 (FIG. 4) and the pins of the output signal are soldered (FIG. 5). FIGS. 6 and 7 show further views of the assembly.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for forming a tuned ultrasound transducer assembly and assembling the tuned ultrasound transducer assembly to a medical device, the medical device having a system side, the method comprising:

selecting a transformer having a plurality of inductance values and voltage gain values, at least one inductance value and voltage gain value of which are appropriate to the operation of a transducer, the transducer having a ceramic side, the transformer having a first plurality of tap lines on a first side of the transformer, and a second plurality of tap lines on a second side of the transformer, each tap line corresponding to said at least one of the plurality of inductance values and voltage gain values;

connecting the transformer to a printed circuit board (PCB) having a first plurality of electrical leads matching the first plurality of tap lines of the transformer and a second plurality of leads matching the second plurality of tap lines; and connecting the medical device system side to one of the first plurality of leads and connecting the transducer-ceramic side to one of the second plurality of leads.

2. The method of claim 1, wherein a transducer is measured for impedance magnitude and phase, and a transformer is selected having a tuning profile sufficiently close to the transducer so as to balance the transducer to a particular impedance and phase angle value.

3. The method of claim 1, wherein the assembly is attached to the transducer.

4. The method of claim 2, wherein the transducer is a mechanically focused high intensity ultrasound transducer.

5. The method of claim 2, wherein the transducer is a 2D or 3D array.

6. The method of claim 1, wherein opening the signal between two or more electrical leads is done by connecting a jumper between the leads.

7. The method of claim 1, wherein opening the signal between two or more electrical leads is done by blowing out a block between the leads.

8. The method of claim 1, wherein opening the signal between two or more electrical leads is done by connecting a mechanical switch between the leads.

9. An ultrasound transducer tuning assembly comprising:

a transformer having a plurality of impedance sections demarked by a like number of taps, each of the impedance sections having a different inductance value and voltage gain value;

a printed circuit board attached to the transformer, wherein the taps connect to a plurality of lands on the PCB, the PCB having a first electrical connection for receiving a first electrical signal and a second electrical connection for transmitting a second electrical signal;

an ultrasound transducer in electronic communication with the second electrical signal; and at least one connector for connecting two lands on the PCB to connect taps on the transformer such that the output signal of the transformer tuning assembly matches a signal profile of the ultrasound transducer.

10. The tuning assembly of claim 9, wherein the ultrasound transducer is mechanically focused.

11. The tuning assembly of claim 9, wherein the ultrasound transducer is electronically focused.

12. The tuning assembly of claim 9, wherein the connector is a jumper.

13. The tuning assembly of claim 9, wherein the connector is a mechanical switch.

* * * * *